United States Patent [19]
Strahilevitz

[11] Patent Number: 5,840,588
[45] Date of Patent: Nov. 24, 1998

[54] AGGLUTINATION INHIBITION ASSAY METHODS AND REAGENTS FOR PSYCHOACTIVE SUBSTANCES

[76] Inventor: Meir Strahilevitz, 10440 Willowdale, Creve Coeur, Mo. 63141

[21] Appl. No.: 469,084

[22] Filed: Jun. 5, 1995

Related U.S. Application Data

[62] Division of Ser. No. 699,159, May 13, 1991, which is a division of Ser. No. 345,964, May 1, 1989, Pat. No. 5,037,645, which is a division of Ser. No. 925,821, Oct. 30, 1986, Pat. No. 4,834,973, which is a division of Ser. No. 319,238, Nov. 9, 1981, Pat. No. 4,620,977, which is a continuation of Ser. No. 761,290, Jan. 21, 1977, Pat. No. 4,375,414, which is a continuation of Ser. No. 255,154, May 19, 1972, abandoned.

[30] Foreign Application Priority Data

May 20, 1971 [GB] United Kingdom ................ 16001

[51] Int. Cl.$^6$ ............ G01N 33/531; G01N 33/543; G01N 33/546; G01N 33/555
[52] U.S. Cl. .............. 436/518; 436/520; 436/521; 436/533; 436/534; 436/547; 436/815; 436/816; 436/822; 530/391.1
[58] Field of Search ............ 435/7.1, 7.9, 7.94, 435/961; 436/518, 520, 521, 523, 527, 529, 533, 534, 536, 538, 804, 815, 816, 822, 901, 541, 542, 547; 530/391.1

[56] References Cited

U.S. PATENT DOCUMENTS

| | | | |
|---|---|---|---|
| 3,088,875 | 5/1963 | Fisk | 436/805 |
| 3,236,732 | 2/1966 | Arquilla et al. | 436/521 |
| 3,639,558 | 2/1972 | Csizmas et al. | 436/521 |
| 3,639,559 | 2/1972 | Tax | 436/543 |
| 3,646,346 | 2/1972 | Catt . | |
| 3,652,761 | 3/1972 | Weetall et al. | 436/527 |
| 3,654,090 | 4/1972 | Schurrs et al. . | |
| 3,690,834 | 9/1972 | Goldstein et al. | 436/816 |
| 3,709,868 | 1/1973 | Spector . | |
| 3,775,253 | 11/1973 | Dieter et al. | 435/180 |
| 3,817,837 | 6/1974 | Rubenstein et al. | 435/7.9 |
| 3,852,157 | 12/1974 | Rubenstein et al. | 436/816 |
| 3,940,475 | 2/1976 | Gross | 436/518 |
| 3,992,631 | 11/1976 | Harte | 436/815 |
| 4,308,026 | 12/1981 | Mochida et al. | 436/523 |
| 4,376,110 | 3/1983 | David et al. | 436/513 |
| 4,663,278 | 5/1987 | Dinello | 435/7.91 |
| 4,828,985 | 5/1989 | Self | 435/7.94 |
| 5,677,132 | 10/1997 | Strahilevitz | 435/7.1 |

OTHER PUBLICATIONS

B. Van K. Weeman et al, *Scand. Juur. Immunol. Supplement*, vol. 7, No. 8, 1978, p. 77.
Williams et al *Methods in Immunologyy and Immunochemistry*, vol. 1, Academic Press, 1967, p. 142.
L. Goodfriend et al, in F. G. Peron et al (Eds.) *Immunologic Methods in Steroid Determination*, Appleton–Century–Crofts, 1970, pp. 31–32.
Adler et al, *Jour. Immunol.*, 106, 1684–1685, 1971.
Butler, Jr., *Jour. Immunol. Meth.*, 7, 1–24, 1975.

(List continued on next page.)

*Primary Examiner*—David Saunders
*Attorney, Agent, or Firm*—Polster, Lieder, Woodruff & Lucchesi

[57] ABSTRACT

Immunoassays of psychoactive drugs including psychotomimetic drugs, narcotic drugs, and tetrahydrocannabinols and treatment methods based on the antigenic properties of protein conjugates of these drugs. These methods are based upon treating the psychoactive substances as haptens and utilizing their protein conjugates to produce antibodies to the psychoactive materials themselves. The immunoassay methods include both agglutination and agglutination-inhibition reactions. The treatment methods include treatment or both exogenous, administered drugs (such as cannabinols, LSD, heroin and morphine) and endogenous substances (such as N,N-Dimethyltryptamine and 5-Methoxy-N,N-Dimethyltryptamine, by active immunization and also passive immunization.

21 Claims, 3 Drawing Sheets

OTHER PUBLICATIONS

Mule et al, *Immunoassays for Drugs Subject to Abuse*, CRC Press, Inc., 1974.

Sevier et al, *Clin. Chem.*, 27, 1797–1806, 1981.

Handbook of Analytical Toxicology, Irving Sunshine, Editor, The Chemical Rubber Company, Publisher; Cleveland, Ohio, 1969.

D.J. Berry et al., Bulletin on Narcotics, vol. 22(3), Jul.–Sep. 1970, United Nations Publication.

Harold V. Street, Journal of Chromatography, vol. 48, pp. 291–294, 1970.

H. Van Vunakis et al., Bioch. Pharmacol., vol. 18, pp. 393–404, 1969. (SIG.).

S. Spector and C. Parker, Science, vol. 168, pp. 1347–1348, 1970 (SIG.).

G.D. Niswender and A.R. Midgley, in: Immunological Methods in Steroid Determination, F.G. Peron and B.V. Caldwell Editors, Appleton–Century–Crofts Pub., New York, pp. 149–173, 1970. (SIG).

L. Levine, in: "Handbook of Experimental Immunology." D.M. Weir, Editor, F.A. Davis Comp. Pub., Philadelphia, pp. 707–719, 1970.

Handbook of Experimental Immunology, D.M. Weir Editor, F.A. Davis Comp., Philadelphia, 1970.

W.J. Herbert, in Reference 8, pp. 720–744. (SIG.).

D.A.J. Tyrrell, in Ref. 8, pp. 782–785. (SIG.).

F. Cua–Lim et al., J. Allergy, vol. 34, pp.142–154, 1968. (SIG.).

Ingraham, Proc. Soc. Exp. Biol. N.Y., vol. 99, p. 452–, 1958. (SIG.).

N.S. Ranadive and A.H. Sehon, Canad. J. Biochem., vol. 45, pp. 1701–1710, 1967.

S. Spector, in: Advances in Biochemical Psychopharmacology, vol. 1, E. Costa and P. Greengard Editors, pp. 181–190, Raven press, New York, 1969. (SIG.).

R.N. Pinckard and D.M. Weir, in Ref. 8, pp. 493–524.

"Immunologic Methods in Steroid Determination." F.G. Peron and B.V. Caldwell Editors, Appleton–Century–Croft, Pub., New York, 1970.

L. Goodfriend and A.H. Sehon, in Ref. 17. pp. 15–21.

M. Strahilevitz et al., Biological Psychiatry, vol. 3, pp. 227–236, 1971. (SIG.).

Fultrope et al., Brit. Med. J., pp. 1049–1054, Apr. 20, 1963.(SIG.).

J.R. Batchelor, in Ref. 8, pp. 988–1008. (SIG.).

E.A. Kabat and M.M. Mayer: Experimental Immunochemistry, p. 124, second edition, Charles C. Thomas, Pub., Springfield, Illinois, 1961.

I.H. Thorneycroft et al., in Ref. 17, pp. 63–81.

G.E. Abraham and W.D. Odell, In Ref. 17, pp. 87–112.

S. Spector, The Journal of Pharmacology and Experimental Therapeutics, vol. 178 (2), pp. 253–258, 1071.

K.J. Catt, In Protein and Polypeptide Hormones, Proceedings of the International Symposium, Leige, M. Margoulis, Editor, Excerpta Medica Foundation Pub. Amsterdam, pp. 639–645, 1969. (SIG.).

D.H. Campbell et al., Proc. Nat. Acad. Sci. USA, vol. 37, pp. 575–578, 1951.

A. Malley and D.H. Campbell, J. Am. Chem. Soc., vol. 85, pp. 487–488, 1963.

H. Van Vunakis, et al., The Journal of Pharacol. and Exp. Therapeutics, vol. 180 (2), pp. 514–521, 1972. (SIG.).

J.D. Teale et al., The Lancet, Sep. 7, 1974, pp. 553–555.

AGGLUTINATION INHIBITION ASSAY METHODS AND REAGENTS FOR PSYCHOACTIVE SUBSTANCES

This is a division of copending application Ser. No. 699,159, filed on May 13, 1991, which is a division of application Ser. No. 345,964, filed May 1, 1989, now U.S. Pat. No. 5,037,645, which is a division of application Ser. No. 925,821, filed Oct. 30, 1986, now U.S. Pat. No. 4,834,973, which is a division of application Ser. No. 319,238, filed Nov. 9, 1981, now U.S. Pat. No. 4,620,977, which is a continuation of application Ser. No. 761,290, filed Jan. 21, 1977, now U.S. Pat. No. 4,375,414, which is a continuation of application Ser. No. 255,154, filed May 19, 1972, abandoned.

BACKGROUND OF THE INVENTION

This invention relates to improved immunoassays of psychotomimetic drugs, narcotic drugs, tetrahydrocannabinols and other psychoactive drugs.

At the present time, there are certain methods used for the determination of psychotomimetic and narcotic drugs in biological materials.

The techniques that are used in the present time for the determination of drugs in biological materials, are described in detail in the *Handbook of Analytical Toxicology* (Irving Sunshine, Editor; The Chemical Rubber Company, Publisher; Cleveland, Ohio, 1969). They include in different combination for the different drugs: paper, thin layer and gas-liquid chromatographic methods, crystal tests, fluorescence, infrared, ultraviolet, thermal microscopy and animal pharmacology studies.

In general, the tests are time consuming, expensive, require expensive equipment, and require well trained personnel. Some of the tests are not sensitive, others lack high specificity. Special difficulty is encountered in the determination of one drug in the presence of other drugs in the same biological material specimen. Thus heroin is difficult to determine in the urine in the presence of nicotine, as disclosed by D. J. Berry et al in "The Detection of Drugs of Dependence in Urine" (Bulletin on Narcotics 22, No. 3, July–September 1970; United Nations Publication). Tetrahydrocannabinols are difficult to determine in the presence of barbiturates, and complicated methods are needed for their determination in the presence of barbiturates, as described by Harold V. Street in "Identification of Drugs by a Combination of Gas-Liquid, Paper and Thin-Layer Chromatography" (Journal of Chromatography 48, 291–4, 1970).

The methods of the present invention have the advantages of simplicity, speed, specificity and low cost. They also have the advantage of being able to be applied "on the spot" (e.g. emergency room of a small field hospital). Van Vunakis et al ("Production and Specificity of Antibodies Directed towards 3,4,5-Trimethoxy-phenyl-ethylamine, and 2,5-Dimethoxy-4-methylamphetamine," Bioch. Pharmacol. 18, 393–404, 1969) were able to obtain high specificity and sensitivity in their determination, by microcomplement fixation inhibition of 3,4,5-Trimethoxy-phenylethylamine and congeners, as well as 2,5-Dimethoxy-4-Methylamphetamine and congeners. Micro-complement-fixation-inhibition is however a complicated method. Reagents have to be prepared freshly for each experiment, and they require specially trained personnel. In the methods hereinafter to be described, no such limitations are present.

The length of time required by presently known procedures for determining psychoactive drugs also severely limits their usefulness in clinical applications.

The invention also includes immunological methods for the treatment of drug intoxication; the treatment and prevention of drug addiction, drug dependence and drug abuse; and the treatment of schizophrenia. The need for treatment methods for intoxication by psychoactive drugs, methods for freeing persons dependent on such drugs from their dependence, and methods of treating schizophrenia has long been felt. The present methods provide attractive and useful approaches to all of these needs.

SUMMARY OF THE INVENTION

In accordance with this invention, generally stated, diagnostic and treatment methods are provided by the use of the haptenic properties of psychoactive material, The term "psychoactive" includes psychotomimetic compounds containing an indol ring such as N,N-Dimethyltryptamine and its congeners and LSD 25 and its congeners; amphetamines and their congeners; narcotics such as phenanthrene alkaloids (such as morphine, heroin, codeine, hydromorphone, and levorphanol) and nonphenanthrene alkaloids (such as meperidine, methadone, and phenazocine); and tetrahydrocannabinols and other cannabinoids.

A hapten may be defined as any small molecule which by itself does not produce antibodies but which, when conjugated to a carrier protein or other macro-molecular carrier, induces in the recipient animal or human the production of antibodies which are specific to the small molecule.

The present invention is based in part upon the application of known immunoassay techniques for haptens to certain psychoactive compounds which have not heretofore been recognized as haptens (such as N,N-dimethyltryptamine and congeners, and tetrahydrocannabinols and their congeners); in part upon the discovery of methods of adapting techniques which were heretofore used only for the determination of antibodies or complete antigens to techniques for determining haptens; in part upon the discovery of immunological treatment methods for such seemingly disparate medical problems as drug intoxication, drug dependence and schizophrenia; and in part upon the development of entirely new methods for the treatment of drug intoxication based in part upon the haptenic characteristics of the intoxicating drugs.

The discovery that 5-methoxy-N,N-dimethyltryptamine and congeners are haptens and the recognition that tetrahydrocannabinols (such as delta-9-tetrahydrocannabinol) are haptens, permits their determination by known immunoassay methods for haptens, such as radioimmunoassay (Spector et al, Science 168, page 1347, 1970; Niswender et al, in *Immunological Methods in Steroid Determination*, edited by Peron and Caldwell, 1970, pages 149–173) and micro-complement fixation inhibition (Levine, in Handbook of Experimental Immunology, edited by D. M. Weir, 1967, pages 707–719, especially page 712). These psychoactive haptens also may be utilized in the determination of their antibodies by methods such as those described in *Handbook of Experimental Immunology* (ed. Weir), pages 423–968, for example hemagglutination (W. J. Herbert "Passive Hemagglutination" in *Handbook of Experimental Immunology*, pages 720–744).

The invention also encompasses the determination of haptens, and particularly psychoactive haptens, by simple and accurate agglutination and agglutination-inhibition assays.

The agglutination inhibition assay includes the steps of mixing a sample containing an unknown quantity of psychoactive hapten with a predetermined quantity of an antibody to the hapten, and then combining this mixture with a predetermined quantity of the hapten bound to an agglutinable particulate carrier. Presence of a sufficient amount of the psychoactive hapten in the sample will inhibit hemagglutination. The usual tray or other equipment may be utilized to obtain a quantitive measure of the psychoactive hapten (*Handbook of Experimental Immunology*, pp 782–785).

The agglutination methods involve the binding of an antibody to an agglutinable particulate carrier. This binding may require the use of a chemical binding technique such as the bis-diazotized-benzidine (BDB) technique. These techniques are set out in *Handbook of Experimental Immunology*, pages 737–740, Cua-Lim et al, J. Allergy 34, 142 (1963); Ingraham, Proc. Soc. Exp. Biol., N.Y. volume 99, 452 (1958).

These agglutinable carrier-bound antibodies may be used in a number of agglutination procedures. In one, a sample is mixed with the agglutinable carrier-bound antibody in suspension, the agglutinable carrier-antibody is then mixed with a free antibody to the hapten. If the sample contains above a minimal amount of the free hapten, agglutination will result. In another method antibodies to two different sites on the hapten are prepared and bound to an agglutinable particulate carrier. Addition of a sample which contains the free hapten produces agglutination. Other procedures utilizing two different antibodies to two different sites on the hapten may be provided in which only one, or neither, of the antibodies is bound to an agglutinable particulate carrier.

In all of the agglutination and agglutination inhibition procedures, erythrocytes (red blood cells) are the presently preferred carrier. The erythrocyte may or may not be treated, for example by formalin treatment (Ingraham, supra). However, other agglutinable material such as latex or other particles may be useful in some or all of the methods.

The invention also encompasses the passive immunization for drug (hapten) intoxication. It is particularly directed to in vitro immunotherapy methods through immunodialysis or immuno-adsorbtion techniques. It also may be applied to auto-intoxication by substances etiological to diseases such as schizophrenia. For example, recent research indicates that N,N-dimethylatedindoleamines are psychotomimetic agents which are etiological to schizophrenia. See for example Tanimukai et al in *Recent Advances in Biological Psychiatry*, volume 10, pages 6–15 (1968); Narasimhachari et al in *Biological Psychiatry* volume 3, pages 21–23 (1971). Therefore, one treatment method includes the passive immunization of schizophrenic patients with antibodies to N,N-dimethylatedindoleamines. Antibody fragments may also be used. The treatment of species which are etiological to schizophrenia and also are complete antigens may include the step of splitting the antibodies (for example by the method set out in Boyd, *Fundamentals of Immunology* (4th edition, 1966), especially at pages 70–71 in order to prevent precipitation of the species. The active immunization procedure may be used both in schizophrenia, by administration of an antigen which produces antibodies to a species which is etiological to schizophrenia (for example a protein conjugate of N,N-dimethyltryptamine), or in the treatment of drug dependent persons. The treatment includes administration of an antigen (or antigens) which produces antibodies to the drug (or drugs) on which the individual is dependent.

DESCRIPTION OF THE PREFERRED EMBODIMENTS

The following examples are illustrative of the methods and materials of this invention.

The following methods are utilized to produce the materials needed to carry out the invention:

a. Conjugation

The psychoactive haptens which contain an immino (NH) group (such as the N,N-dimethylated indolamines and LSD) are conjugated to Human Serum Albumin (HSA) using the Mannich formaldehyde reaction, as described by Ranadive and Sehon, Canad. J. Biochem, 45, p 1701 (1967). The conjugation in this method is to the immino (NH) group. Other hapten-macromolecular conjugates are formed by standard methods, for example those set out in Spector, in *Advances in Biochemical Psychopharmacology*, volume 1 (ed. Costa and Greengard) p 181 (1969); Pinckard et al in *Handbook of Experimental Immunology*, p 493; and Goodfriend et al in *Immunologic Methods in Steroid Determination*, p 15; and Ingraham, supra.

Determination of conjugation is done following the method described in Strahilevitz et al, *Biological* Psychiatry 3, 227 (1971), by a spectrofluorometric method.

b. Production of Antibodies to Haptens

Immunizations of rabbits with conjugates in complete Freund's Adjuvant are carried out by a similar procedure to the one described by Strahilevitz et al, supra. The preparation of antisera and globulin fractions are also described in this reference. The antibodies may be purified by known methods such as those set out in *Immunologic Methods in Steroid Determination*.

c. Preparation of Erythrocytes (Agglutinable Particulate Carrier)

Preparation of formalinized, type O human erythrocytes is done according to the methods described by Ingraham, supra. Some cells prepared by this method can be used even 15 months after preparation.

d. Binding of Haptens to Erythrocytes

Conjugation of haptens to the formalinized erythrocytes is done by the Bis-Diazotized-Benzidine technique (BDB technique).

Figure 1:
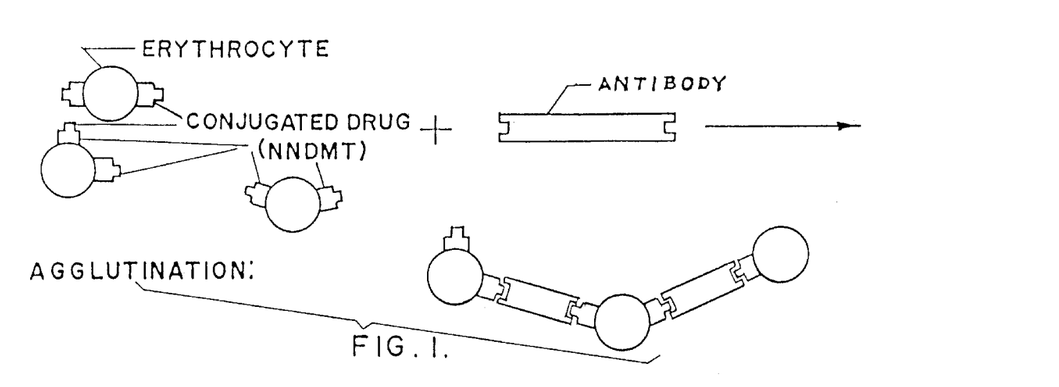
FIG. 1 is a diagrammatic representation of a hemagglutination inhibition procedure utilized in the methods of the present invention.

Determination of presence of antibodies in the rabbit serum and determination of their specificity and cross reactivity in the serum of the drug-HSA-conjugate immunized rabbits is done by hemagglutination of the drug bound erythrocytes by their specific antisera and by specific inhibition of the hemagglutination in the presence of the free drug (hapten inhibition in the presence of the free drug) (see Fultrope et al, Brit. Med. J., Apr. 20, 1963, pp 1049–54). The hemagglutination procedure is shown diagrammatically in FIG. 1. For example, inhibition of hemagglutination by NNDMT but not by other drugs will indicate presence of antibody specific to NNDMT. Determination of presence of specific antibodies is also done by double diffusion and double diffusion inhibition studies (i.e. inhibition of the precipitation in the presence of the free drug as described by Ranadive and Sehon, supra, for Serotonin).

EXAMPLE 1

Radioimmunoassay of Tetrahydrocannabinols

A tetrahydrocannabinol is conjugated to a protein by one of the standard methods utilized to bind steroids to proteins (*Immunologic Methods in Steroid Determination*). The conjugate is prepared in such a way as to produce a ratio of tetrahydrocannabinol to carrier molecule of from 4:30 to 30:1. The conjugate is emulsified in a phosphate buffer saline (pH 7.4). Rabbits, sheep or other suitable animals are immunized with from about ½–2 mg of the conjugate per kilogram body weight (in concentration of about 5 mg/ml PBS) in equal volume mixture with complete Freund's adjuvant. The mixture is again emulsified before injection into multiple sites, e.g. intradermally, into the foot pad, subcutaneously, and intra-peritoneally. Injections are made once every two weeks and blood taken from the animal, allowed to clot, and tested for antibodies, as set out in Ranadive and Sehon, supra.

Radioactively labeled ($^3$H) tetrahydrocannabinol (obtained from National Institute of Mental Health) in a predetermined amount, is added to the antibody to the tetrahydrocannabinol. Ammonium sulfate (or another precipitating reagent) is then added in order to precipitate the tetrahydrocannabinol-bound antibody. The precipitate is sedimented by centrifugation and washed. The precipitate is then dissolved with a suitable solubilizing reagent (such as Tween 80 or NCS solubilizer [Amersham/Searle]). A standard curve is prepared by adding to the test solution varying amounts of unlabeled tetrahydrocannabinol to the predetermined amount of labeled tetrahydrocannabinol. The quantity of tetrahydrocannabinol in a sample is then determined by addition of the sample (e.g. serum) together with the predetermined quantity of labeled tetrahydrocannabinol and antibody. Comparison of the radioactivity count of the precipitate with the standard curve yields the amount of tetrahydrocannabinol in the sample.

EXAMPLE 2

Radioimmunoassay of 5-methoxy-N,N-dimethyltryptamine

Antibodies to 5-methoxy-N,N-dimethyltryptamine (5-MeO-N-DMT) are prepared according to the method of Strahilevitz et al, supra. 5-MeO-N-DMT is conjugated to a radioactive ($^{131}$I) protein. Radioimmunoassays are carried out using the radioactive hapten-protein conjugate, in the same manner as in EXAMPLE 1.

In EXAMPLES 1 and 2 radioimmunoassay can be modified by using the "double antibody procedure" as described by Niswender et al in *Immunological Methods in Steroids Determination*, p149. In EXAMPLE 1, non-labeled tetrahydrocannabinol may be conjugated to $^{131}$I-rabbit serum albumin, or to another radioactive labeled protein carrier for the purpose of being used in the radioimmunoassay procedure instead of the radioactive $^3$H tetrahydrocannabinol.

EXAMPLE 3

Detection of a Specific Psychoactive Drug by a Qualitative Test

Figures 2, 2A, 3:
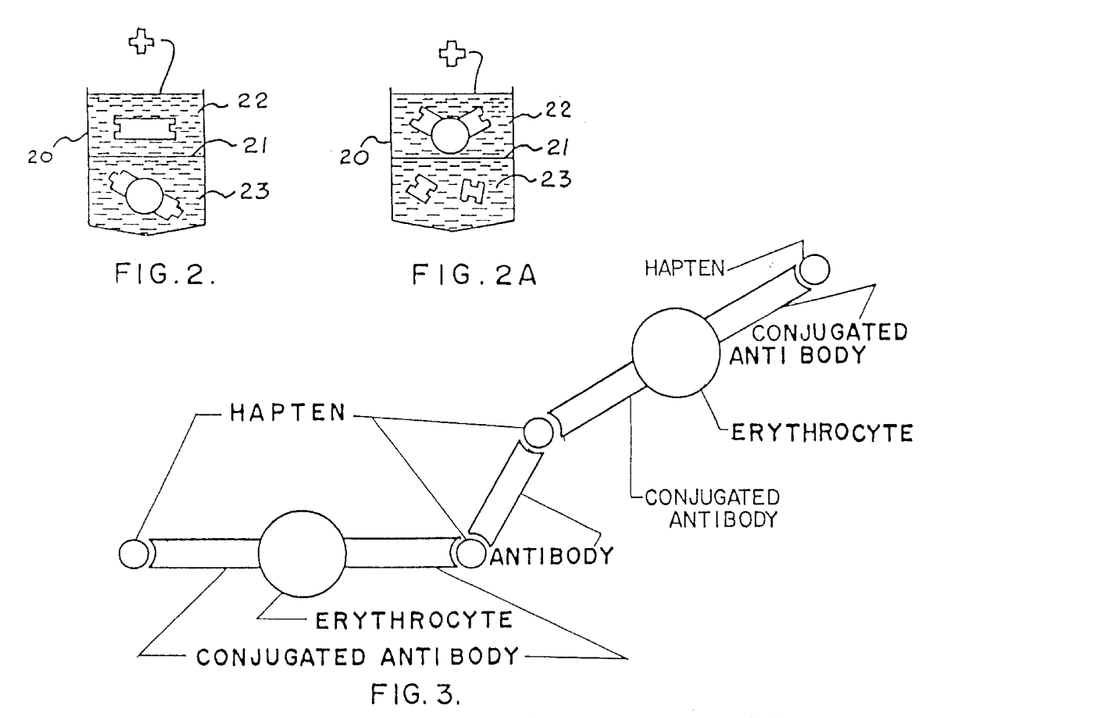
FIG. 2 is a diagrammatic representation of a test system of Examples 3 and 4 of the present invention.
FIG. 2A is a diagrammatic representation of a test system of Examples 5–7 of the present invention.
FIG. 3 is a diagrammatic representation of a hemagglutination reaction of the test system of Example 5 of the present invention.

By titration, a suitable amount of antiserum specific to a drug and red cells to which this drug is conjugated, is determined. As shown in FIG. 2, tubes 20 made of plastic with a thin plastic divider 21 are used for this test system. If the drug in question is present in the sample that is being examined, as a free hapten, it will combine to the antibodies against it after the sample is introduced into the upper compartment of the tube and incubated for 15 minutes at 37° C. When, after incubation as described above, the thin plastic barrier 21 in the middle of the tube 20 is broken by the needle with which the sample was put into the upper compartment 22, and the mixture of serum sample tested and the drug specific antiserum is allowed to mix with the drug-conjugated erythrocytes in the lower compartment of the tube, the presence of at least a particular quantity of the drug (or a particular range of quantities) will inhibit or prevent agglutination of the drug-conjugated erythrocytes. Thus agglutination inhibition will be an indication of the presence of free drug in the sample tested. (If the drug is carried in the serum, on a macromolecule like protein, or another macromolecular carrier, then it will be a complete antigen and precipitation may occur while the drug is incubating in the upper compartment 22 of the tube with the specific antiserum. However, hemagglutination inhibition should in addition be demonstrated in the lower compartment 23 of the tube.)

EXAMPLE 4

Quantitive Determination of Drugs

This is done with a tray similar to the one that is used routinely for microhemagglutination studies (see Tyrell, supra).

Serial dilutions of the tested serum is added to the upper compartment by a small syringe. The difference between the tray used for this test and the one that is being used routinely, is that the tray with the cylinders will be higher, and that each cylinder has an upper and a lower compartment divided by a thin plastic divider (as shown schematically in FIG. 2). The procedure is otherwise identical with the one previously described in EXAMPLE 3. The drug "titer" is the highest dilution in which hemagglutination will be inhibited.

Quantitive determination may also be done by the use of routinely used trays and loops used for microhemagglutination and microhemagglutination inhibition.

This method can be used for the determination of a wide variety of psychoactive haptens, including the N,N-dimethylated indolamines, LSD, narcotics (like heroin or morphine) and tetrahydrocannabinols, and may in principle be applied to determining any haptenic chemical or normal or pathological haptenic body metabolite.

In the above described quantitive methods, with each unknown serum sample that will be tested for the presence of drugs, a known control negative sample, and a known positive sample, that will include a known amount of drug, will be done simultaneously.

EXAMPLE 5

Qualitative Determination of Drug-Hapten by Reversed BDB Technique

Presence of Drug-Hapten in this system will be detected by hemagglutination.

As shown in FIG. 2A, tubes 20 are the same as for EXAMPLE 3. Antibody to the drug-hapten is prepared in an identical way as described in EXAMPLES 3 and 4. The anti drug-hapten antibodies are conjugated to the formalinized erythrocytes as described by Cua-Lim et al, supra, in the Reversed BDB technique. They are then placed in the upper compartment 22 of the tube. Free antibodies to the drug-hapten are included in the lower compartment 23 of the tube 20. The material tested for free drug-hapten is then injected into the upper compartment 22 and incubated. If free drug-hapten is present it will be bound to the anti-drug-hapten-antibodies which are conjugated to the erythrocytes. After the incubation, the tube is centrifuged and the red cells in the upper compartment are washed with Phosphate Buffer Saline PH 7.4 (PBS). The thin plastic divider 21 is then pierced by the needle and the material drops into the lower compartment 23. If drug-hapten is present attached to the anti-drug-hapten-antibodies that are conjugated to the erythrocytes, then hemagglutination appears indicating presence of free drug in the sample.

This is shown schematically in FIG. 3.

The method has the advantage of indicating the presence of hapten by hemagglutination rather than by hemagglutination-inhibition.

EXAMPLE 6

Quantitative Determination of Drug-Hapten by Reversed BDB Technique

The same technique described in EXAMPLE 5, is utilized for quantitative determination of drug-hapten, utilizing the tray and the other methods as described in EXAMPLE 4. Here again the presence of free-drug-hapten is indicated by hemagglutination.

Addition of material containing free hapten to the upper compartment 22 and then incubated causes the hapten-drug to bind to the formalinized erythrocyte bound antibody, and in the presence of unbound anti drug-hapten antibody, agglutination will take place in the lower compartment 23.

The foregoing methods (EXAMPLES 3–6) can be adapted for use in non-animal materials such as plant materials and drug samples, as can the following two EXAMPLES.

EXAMPLE 7

Qualitative Determination for the Presence of One Drug out of a Group of Drugs This method utilizes a test system similar to the test system described in EXAMPLE 5. The system is identical with the exception that in the upper compartment 22, a mixture of several batches of formalinized erythrocytes is present, each batch being conjugated with an antibody to a different drug-hapten.

Similarly the lower compartment 23 contains a mixture of unbound antibodies, identical with those present in the upper compartment 22. If the antibodies, present in a free form in the lower compartment 23 and conjugated to the erythrocytes in the upper compartment 22, are specific against drugs: A, B, C, D, E . . . and if any one of these drugs or some of these drugs is present in the tested sample, a positive reaction, indicated by a hemagglutination, will be visible in the lower compartment 23 thus indicating that one or more of the drugs A, B, C, D, E . . . are present in the sample.

A detailed analysis for specific drugs as described above will determine the specific drug or drugs which are present in the tested sample.

EXAMPLE 8

Production and Use of Antibodies to Different Sites on a Hapten

In the foregoing EXAMPLE, in order to ensure that the hapten will have at least two combining sites to combine with the antibodies, the hapten can be conjugated to the carrier protein (or another macromolecular carrier) through two different sites in the hapten molecule. For example, with estrone, conjugation will be done to rings A and D respectively in the estrone molecule by the methods described by Goodfriend and Sehon in *Immunological Methods in Steroid Determination,* supra. Conjugation to two different sites in the hapten with protein, can be done in various haptens by a variety of conjugation methods. The two conjugates of the hapten (in the example the protein conjugates of Estrone through ring A and D respectively) will be used for immunization of animals (such as rabbits). (Immunization with each of the conjugates is preferably done in different rabbits.) It is expected that the immunized rabbit will produce antibodies directed towards an antigenic site on the estrone or other hapten molecule which is sterically guided by the site on the molecule through which conjugation to the protein was done. Generally the antibody will be directed toward a site away from (complementary to) the comjugated protein. Besides using different conjugation methods, other methods by which usefully different antibodies to the same hapten may be produced include the use of antibodies to the conjugate of the hapten with two different carriers, like HSA (human serum albumin) and hemocyanin or other two different carriers. Either the same method of conjugation or different methods of conjugation can be used for conjugating the hapten to the two different carriers. Each one of the two antisera may then be specific against another antigenic site on the hapten molecule. The same result may be obtained or enhanced by actively immunizing different animal species (such as sheep and rabbits) with the hapten-protein conjugate or conjugates to produce the first and second antibodies.

Figure 4:
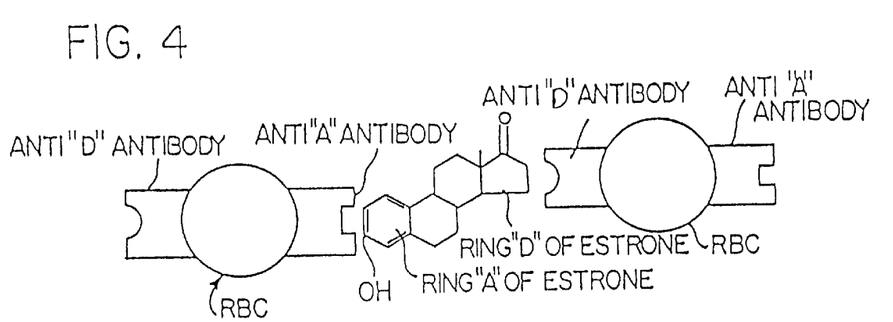
FIG. 4 is a diagrammatic representation of an agglutination reaction of a test system of Example 8 of the present invention.
Figure 5:
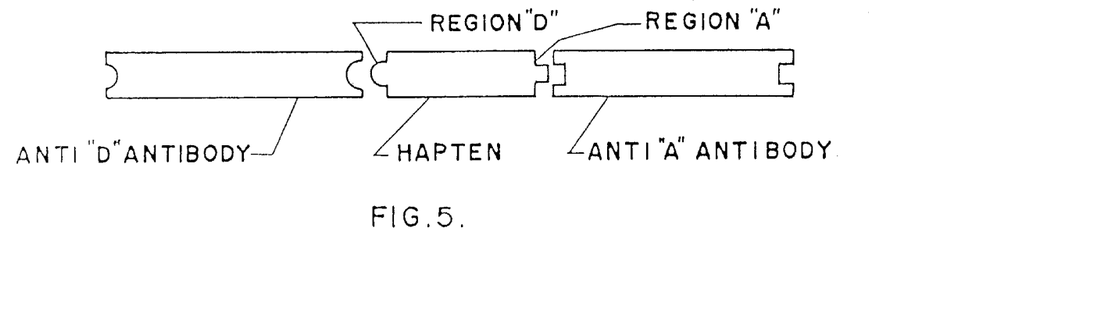
FIG. 5 is a diagrammatic representation of a precipitation reaction of a test system of Example 8 of the present invention.

The antibodies to two hapten sites may be used in a number or procedures, as follows:

a. Both antibodies are conjugated to red blood cells (RBC) or other agglutinable-particulate carrier like latex and placed in suspension, as in the preceding example, in a container. As shown in FIG. 4, in the presence or free hapten in the test material (e.g., free estrone) an antigenic site on the ring A of the estrone will attach itself to the antibody produced against the protein conjugate which was conjugated with estrone through ring D. Similarly, an antigenic site on ring D of estrone will attach itself to the antibody produced against the protein conjugate which was conjugated with estrone through ring A. Therefore, the presence of at least a certain amount (i.e. a certain range) of hapten in a sample will produce agglutination.

b. As shown in FIG. 5, with the use of anti A and anti D antibodies in the test system estrone can be demonstrated by precipitation in fluid or solid media. Other haptens as well can be determined by precipitation in the presence of antibodies to two different antigenic sites in the hapten.

c. Other procedures may use combinations of antibodies which are bound to agglutinable particles and antibodies which are not so bound. Also, more than two different antibodies may be used.

All of the foregoing hemagglutination tests can be used in the presence of developing agents such as polyvinylpyrolidone (P.V.P.) or Dextran in order to increase their sensitivity. (*Handbook of Experimental Immunology,* p. 995).

EXAMPLE 9

Active Immunization Treatment of Schizophrenia

Active immunization treatment of schizophrenia is carried out with a conjugate of a psychotomimetic compound (or a combination of conjugates of such compounds) such as N,N-dimethyltryptamine, 5-methoxy-N,N-dimethyltryptamine, tryptamine, and other psychotomimetic haptens, the presence of which has been described in the biological materials of schizophrenic individuals. These psychotomimetic small molecules are conjugated with protein macromolecular carrier, or with polyamine acid molecules as carriers (like: polylysine or polyarginine).

Immunization of the patient is carried out either without the use of adjuvant or with the use of an adjuvant. This will be tried in humans only after the safety of the compound, safety of the route of immunization, schedule of immunization, and the safety of the adjuvant used if any, has been extensively studied, and determined in studies in experimental animals, by suitable methodology which is available at the present time.

Treatment of schizophrenia by active immunization with complete antigens (immunogens) that may be etiological in the disease (either protein or other complete antigens (immunogens), will include immunization with enzymes that may be etiological in schizophrenia like: indoleamine N methyl transferase, indoleamine O methyl transferase, catechol amine N methyl transferase, catechol amine O methyl transferase as well as other enzymes that may be related to the etiology of schizophrenia.

EXAMPLE 10

Treatment of Schizophrenia by a Passive Immunotherapy Method

Immunization of the patient is carried out by administering antibodies to species which are etiological to the disease. For example, in acute schizophrenia, antibodies to 5-methoxy-N,N-dimethyltryptamine may be administered.

In passive immunization treatment with antibodies against complete antigens present in schizophrenia serum, in order to avoid possible precipitation of the complete antigens by the antibodies, the anitbodies may be treated in such a way as to make them "univalent", for example by mild reduction with dilute HCl and breaking of the antibody molecule into two identical halfs each with one combining site (William C. Boyd, *Fundamentals of Immunology* 4th edition, Interscience Publishers New York, London, Sidney, 1966 pp 70,71). Other methods for obtaining "univalent" non-precipitating antibody, that can yet bind the antigen and possibly neutralize it are also summarized in this reference and can be utilized.

EXAMPLE 11

Treatment of Drug Dependence by Active Immunization

The immunization of drug dependent individuals is in principle similar to the immunotherapy of schizophrenia by active immunization with protein conjugates of methylated indoleamines. The drug or drugs on which the individual is dependent are conjugated to a protein or other macromolecular carrier, for example by one of the methods discussed hereinabove. After the individual is withdrawn from the drug (for example by methadone withdrawal, for heroin), he will be immunized by administration of the conjugate, in a manner similar to that used for the active immunization treatment of schizophrenia.

Many conditions require the removal of species from the blood of an individual under circumstances which make active immunization and even passive immunization treatments (as well as other treatment methods) impractical. Examples of such conditions are severe intoxication (such as with phenothiazines) and certain acute schizophrenic conditions (such as acute catatonic stupor). In Addition, methods are needed for removal, from the circulation of a patient having a malignant tumor, of certain antibodies against tumor-specific antigens. These specific antibodies are known to be "enhancing antibodies" (which stimulate the growth of the tumor). Removal of these antibodies may be therapeutic for such patients. The removal of antibodies which may be etiological in certain allergic conditions or autoimmune diseases is expected to be therapeutic for these conditions. These antibodies include the antibodies specific to the septal region of the brain, e.g. "Taraxein", which according to findings of Heath et al (Am. J. Psychiat., 124, p 1019, (1968); Arch Gen. Psychiat., 16, pl (1967)) are etiological in schizophrenia. It also may be desirable to remove from the circulation of schizophrenic patients other proteins such as the alpha-2 globulin which was found by Frohman et al (Ann. N.Y. Acad. Sci., 96 p 438 (1962)) in schizophrenic patients and which may be etiological in schizophrenia. In all of these conditions, one or both of the following two EXAMPLES may provide an effective treatment.

EXAMPLE 12

Immunodialysis Treatment Primarily for Drug Intoxication

Figure 6:
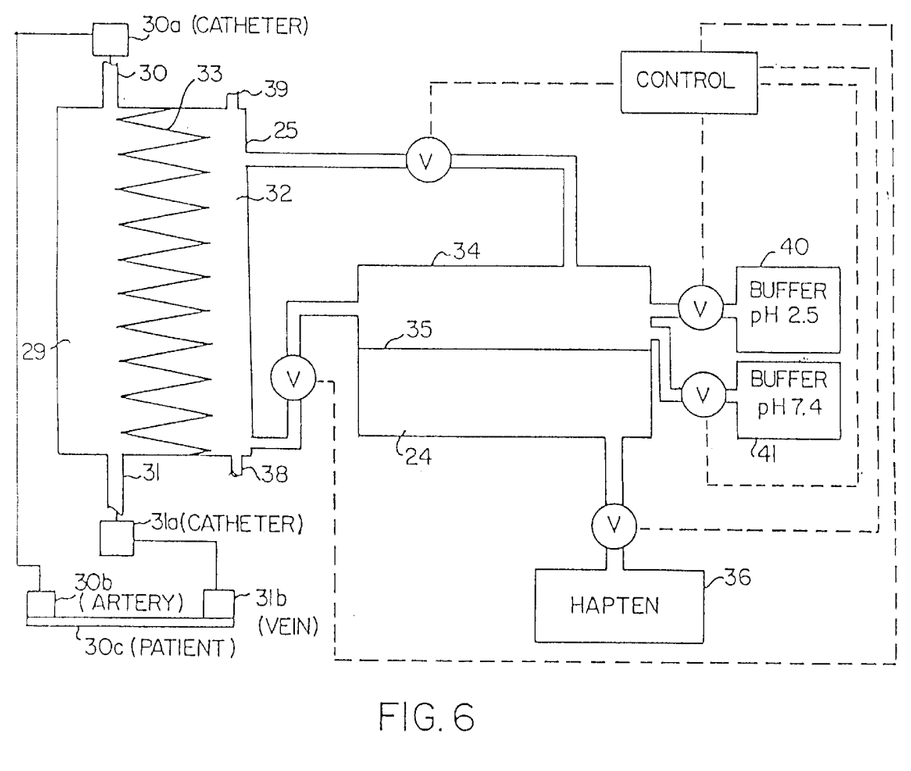
FIG. 6 is a diagrammatic representation of an immunodialysis system of Example 12 of the present invention.

This system is particularly well adapted for the removal of haptens from the circulatory system. All of the apparatus, compartments therein and the materials used with it are of course sterile. In brief, as shown in FIG. 6, a column 25 is divided into a first compartment 29 and a second compartment 32 by a semipermeable membrane 33. Such membranes, having various pore sizes, and thus which are permeable to molecules of various sizes are commercially available. The first compartment 29, an inlet 30 for a catheter 30a which is to be connected to an artery 30b of the patient 30c to be detoxified or otherwise treated, and an outlet 31 connected to a catheter 31a which is to be connected to a vein 31b of the patient 30c, together comprise a blood flow passage through the column 25. The second compartment 32 includes the heterologous antibody directed against the hapten which is to be removed. The antibody is contained in an isotonic solution or other solution such as those used in conventional dialysis treatment ("artificial kidney"). If the hapten is not known, (as in a patient suffering from an overdose of an unknown psychoactive drug), the solution in the second compartment 32 may include a mixture of antibodies to drugs which may be implicated. The semipermeable membrane is folded or pleated so that the surface area of interaction between the patient's blood and the antibody to the drug in the compartment 32 will be as great as possible. The semipermeable membrane is chosen to be of such a porosity and permeability as to be permeable to small molecules like the intoxicating hapten of interest, but is not permeable to large molecules present in the blood of the patient such as serum proteins.

Because the antibodies specifically bind drug molecules that diffuse from the blood of the patient in compartment 29 to compartment 32 through the semipermeable membrane 33, a continuous gradient is present for this intoxicating drug in the patient's blood that therefore continues to diffuse from compartment 29 to compartment 32 as long as compartment 32 includes antibodies directed against the intoxicating drug which are free to bind molecules of the intoxicating drug.

The dialysis system, thus far described, has great advantages over simple blood dialysis, in that it is more specific, and, because of the high speed of binding of free hapten by the antibody to it, the system will generally require a smaller apparatus, and the time for detoxification will be much shorter than required by the use of simple dialysis ("artificial kidney"). The chance of saving the patient's life will therefore be increased. It may also be possible to use vein to vein catheterization of the patient rather than arterial catheterization because detoxification will be accomplished faster.

When the dialysis system thus far described has been used until the antibody is exhausted for practical use, the solution of the antibody-bound hapten may be removed through a drain 38, and fresh antibody solution is added immediately through filler opening 39. The used antibody-bound hapten may be regenerated for use by the following steps: addition of glycine phosphate buffer, pH 2.5 to separate the hapten from the antibody; repeated washings with glycine buffer, each time filtering the solution by a positive pressure system through a semipermeable membrane which is permeable to all of the solution except the antibody; addition of PBS-buffer, pH 7.4 to the free antibody; and sterilization of the antibody solution by passing it through a bacterial filter, i.e. one which is permeable to the antibody but not to bacteria. The solution is then ready to be reintroduced to the chamber 32. This regeneration of the system makes it far more economical than it otherwise would be.

As shown in FIG. 6, the system may also be automatically regenerated, thereby maintaining its efficiency continuously if desired, and in any case simplifying the maintaining of the sterility of the system. In this system, the hapten-antibody is withdrawn from the second chamber 32 and delivered to a first chamber 34 of a cleaning column. Glycine phosphate buffer pH 2.5 is added from a container 40 and differential pressure is applied to accelerate migration of the free hapten across a semipermeable membrane 35 into a second chamber 24 of the cleaning column. The hapten is drained in solution into a reservoir 36, for disposal or subsequent recovery and testing. The free antibody solution is then returned to a pH of 7.4 by the addition of phosphate buffer saline from container 41. The free antibody is then ready to be returned to the second chamber 32 of the column 25. The entire process of regenerating the antibody may be controlled automatically by known differential pressure, valving and control equipment.

EXAMPLE 13

Immunoadsorption Treatment

Figure 7:
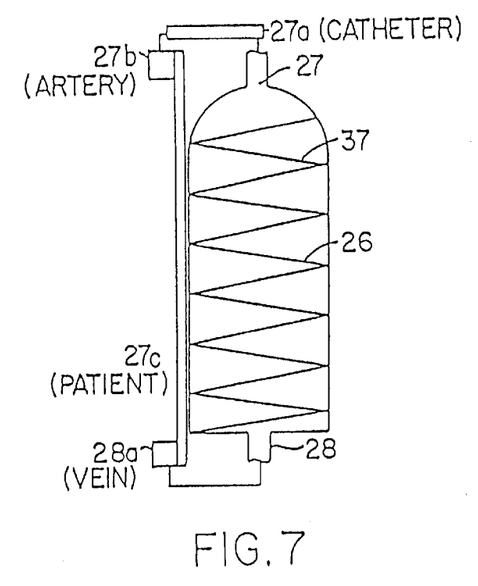
FIG. 7 is a diagrammatic representation of an immunoadsorption system of Example 13 of the present invention.

This treatment system is adaptable to the removal of virtually any reactive species in the blood, but is particularly well adapted to, and described herein with reference to, the removal of haptens, complete antigens, and antibodies by immunological processes. As shown in FIG. 7, the apparatus for this method consists of a column 26 which includes a matrix 37 to which a binding species is linked. The binding species is a hapten, antigen (including a hapten conjugated to a carrier) or antibody which reacts specifically with the species which is to be removed from the blood. The linkage of the binding species to the matrix 37 may preferably be directly to the matrix, as when the matrix is made of a synthetic polymer such as polystyrene-latex. The linkage may also be through a suitable solid phase coating on the matrix. The antibody is then linked to the coating by one of the known methods for the preparation of immunoadsorbents, for example by a modification of one of the methods of Campbell (Campbell et al, Proc. Nat. Acad. Sci., U.S.A., 37 p. 575 (1951); Malley and Campbell, J. Am. Chem. Soc. 85, p. 487 (1963)). If any chance exists that the solid phase adsorbent may break loose from the matrix 37, suitable filters are necessary in the system. The matrix may simply be the wall of the (plastic) column if the length of the column is sufficient to provide the required surface area for interaction at the blood-binding species interface. Preferably, the matrix 37 provides a very large surface area. Such matrices include a spiral structure, as shown in FIG. 7, which requires the blood to travel in a thin layer over a large surface. Other matrices include a honeycomb (open porosity) matrix and a fill of plastic beads.

The upper part 27 of the column 26 is connected with tubing to a catheter 27a that is connected to an artery 27b of a patient being treated and the lower end 28 of the column is connected to a vein 28a of the patient 27c being treated. The blood of the patient flows through the column and the species in the blood to which the binding species is specific becomes bound to the binding species, hence to the matrix. Therefore, the blood which flows from the column 26 is relatively free of the species sought to be removed.

When the column 26 has been removed from the patient, it may be renewed by elution of the species which is bound to the binding species, by known techniques, such as washing with glycine phosphate buffer, pH 2.5.

Numerous variations in the materials, devices and methods of this invention, within the scope of the appended claims, will occur to those skilled in the art in light of the foregoing disclosure.

Having thus described the invention, what is claimed and desired to be secured by Letters Patent is:

1. A method of determining a psychoactive hapten, comprising a step for binding said hapten to an agglutinable particle selected from the group consisting of erythrocytes and latex particles; and thereafter an agglutination inhibition immunoassay step, utilizing said hapten bound to said particle, for the determination of said hapten in a sample.

2. A method determining a hapten selected from the group consisting of psychoactive drugs and metabolites of psychoactive drugs, the method comprising an agglutination inhibition immunoassay for the determination of said hapten in a sample, the immunoassay being carried out with an antibody to said hapten, said antibody having been produced by a step for conjugating said hapten to macromolecule to form a conjugate and a step utilizing said conjugate for producing said antibody to said hapten.

3. A method of determining a psychoactive hapten in a sample comprising a step for mixing the sample with a predetermined quantity of an antibody to said hapten; and thereafter a step for combining said antibody with a predetermined quantity of said hapten bound to an agglutinable particulate carrier, said quantities of said antibody and said carrier-bound hapten being chosen to produce agglutination when and only when the quantity of hapten in said sample is below a predetermined amount.

4. An analytical reagent comprising an antibody to a psychoactive hapten bound to an agglutinable particulate carrier selected from the group consisting of erythrocytes and latex particles.

5. An analytical reagent comprising a psychoactive hapten bound to an agglutinable particulate carrier selected from the group consisting of erythrocytes and latex particles.

6. The reagent of claim 5 wherein the psychoactive hapten is selected from the group consisting of tetrahydrocannabinols, psychotomimetics, and narcotics.

7. The reagent of claim 6 wherein the psychoactive hapten is a narcotic.

8. The reagent of claim 7 wherein the narcotic is selected from the group consisting of morphine and heroin.

9. The reagent of claim 6 wherein the psychoactive hapten is a tetrahydrocannabinol.

10. The reagent of claim 6 wherein the psychoactive hapten is a psychotomimetic.

11. The reagent of claim 10 wherein the psychotomimetic contains an indole ring.

12. The reagent of claim 5 wherein the psychoactive hapten is an amphetamine.

13. The reagent of claim 5 wherein the psychoactive hapten contains an imino group.

14. A method of determining a hapten selected from the group consisting of psychoactive drugs and metabolites of psychoactive drugs, the method comprising a step for binding said hapten to an agglutinable particle selected from the group consisting of erythrocytes and latex particles; and thereafter an agglutination inhibition immunoassay step, utilizing said hapten bound to said particle, for the determination of said hapten in a sample.

15. The method of claim 14 wherein the hapten is selected from the group consisting of tetrahydrocannabinols, psychotomimetics, narcotics, and metabolites of tetrahydrocannabinols, psychotomimetics, and narcotics.

16. The method of claim 14 wherein the hapten is a narcotic or a metabolite of a narcotic.

17. The method of claim 14 wherein the hapten is an amphetamine or a metabolite of an amphetamine.

18. The method of claim 14 wherein the hapten is a tetrahydrocannabinol or a metabolite of a tetrahydrocannabinol.

19. The method of claim 14 wherein the hapten is a psychotomimetic or a metabolite of a psychotomimetic.

20. The method of claim 19 wherein the hapten contains an indole ring.

21. A method of determining a phychoactive hapten, the method comprising an agglutination inhibition immunoassay for the determination of said hapten in a sample, the immunoassay being carried out with antibodies to said hapten, the antibodies having been produced by a step for conjugating said hapten to a macromolecule to form a conjugate and a step utilizing said conjugate for producing said antibodies to said hapten.

* * * * *